United States Patent [19]
Hattori et al.

[11] Patent Number: 6,060,613
[45] Date of Patent: May 9, 2000

[54] PROCESS FOR PRODUCING N-LONG-CHAIN ACYL ACIDIC AMINO ACIDS OR SALTS THEREOF

[75] Inventors: Tatsuya Hattori; Kiyomiki Hirai, both of Yokkaichi, Japan

[73] Assignee: Ajinomoto Co., Inc., Tokyo, Japan

[21] Appl. No.: 09/019,367

[22] Filed: Feb. 5, 1998

[30] Foreign Application Priority Data

May 2, 1997 [JP] Japan .................................. 9-022708

[51] Int. Cl.⁷ .................................................. C07C 231/00
[52] U.S. Cl. .................................................. 554/69; 554/68
[58] Field of Search ........................................ 554/69, 68

[56] References Cited

U.S. PATENT DOCUMENTS

| | | |
|---|---|---|
| 2,463,779 | 3/1949 | Kester . |
| 5,334,713 | 8/1994 | Hattori et al. . |
| 5,529,712 | 6/1996 | Sano et al. . |

FOREIGN PATENT DOCUMENTS 2 015 075   10/1970   Germany .

OTHER PUBLICATIONS

Chemical Abstracts, vol. 80, No. 11, Mar. 18, 1974, AN 60208k, JP 48–035058, Oct. 25, 1973.
Database WPI, Derwent Publications, AN 76–25161X, JP 51–019717, Feb. 17, 1976.
Database WPI, Derwent Publications, AN 88–312208, JP 63–230630, Sep. 27, 1988.
Patent Abstracts of Japan, vol. 12, No. 333 (C–526), Sep. 08, 1988, JP 63–096161, Apr. 27, 1988.

*Primary Examiner*—Deborah D. Carr
*Attorney, Agent, or Firm*—Oblon, Spivak, McClelland, Maier & Neustadt, P.C.

[57] ABSTRACT

Provided is an industrially advantageous process for producing an N-long chain acyl acidic amino acid by condensing an acidic amino acid with a long chain fatty acid halide in water in the presence of an alkali, wherein the reaction is performed in the presence of a polyhydric alcohol. The desired product is obtained in a high yield without the problems of odor and of safety owing to organic solvents and catalyst remaining in the desired product. The equipment for removal of the solvents is reduced, and production is simplified.

20 Claims, No Drawings

PROCESS FOR PRODUCING N-LONG-CHAIN ACYL ACIDIC AMINO ACIDS OR SALTS THEREOF

FIELD OF THE INVENTION

The present invention relates to a process for producing N-long-chain acyl acidic amino acids or salts thereof. More specifically, the present invention relates to a process for reducing N-long-chain acyl acidic amino acids or salts thereof by reacting an acidic amino acid such as glutamic acid, aspartic acid or the like, or its salt with a long-chain fatty acid halide.

DISCUSSION OF THE BACKGROUND

N-long-chain acyl acidic amino acids, for example, an N-long-chain acyl glutamic acid, N-long-chain acyl aspartic acid or salts thereof such as sodium salts, potassium salts, triethanolamine salts and the like have been used as various agents such as detergents, dispersing agents, emulsifying agents, antibacterial agents and the like because they have surface activating action, sterilizing action and the like. N-long-chain acyl acidic amino acids or salts thereof are less irritating to the skin and the hair, and have therefore found wide acceptance in detergent compositions such as hair shampoos, body shampoos and the like.

As a method of forming an N-long-chain acyl acidic amino acid, for example, an N-long-chain acyl glutamic acid, a method is known in which glutamic acid is condensed with a long chain fatty acid halide in a solvent of water in the presence of an alkali (e.g., see Reference Example at the beginning of column 7 in Japanese Patent Publication No. 35,058/1973). However, this prior art method is not said to be a method which can satisfactorily be used industrially because of the low yield.

As a method of producing an N-long-chain acyl acidic amino acid in a high yield, a method is known in which the reaction is conducted in a solvent of water using a tertiary amine or a quaternary ammonium salt as a catalyst (Japanese Patent Publication No. 35,058/1973). However, because these catalysts may irritate skin, eyes, mucous membranes, etc. and also produce an unpleasant odor, a procedure and equipment for removing these catalysts remaining in the desired product are required. Thus, this method is not said to be an industrially satisfactory method.

As another method to increase the yield, a method is known in which a mixed solvent comprised of an organic solvent such as acetone, methyl ethyl ketone, dioxane, tetrahydrofuran or the like and water is used as a reaction solvent (Japanese Patent Publication No. 8,685/1979). However, the use of organic solvents poses health and safety hazards and requires special equipment in order to meet health and safety regulations which in turn causes extra operating costs to be incurred. Therefore, in view of the health and safety related issues, skin irritation, and odor associated with the use of organic solvents, equipment for removing them from the final product is required.

Likewise, a method is known in which a hydrous lower alcohol is used as a reaction solvent to increase the yield (Japanese Patent Publication No. 38,681/1976). However, this method also yields a product which has an undesirable odor due to the lower alcohol remaining in the final product, and a procedure for removing the same is required.

SUMMARY OF THE INVENTION

It is an object of the present invention to provide a process in which an N-long-chain acyl acidic amino acid can be produced from an acidic amino acid and a long chain fatty acid halide in a high yield without the above-mentioned problems.

Under these circumstances, the present inventors have assiduously conducted investigations, and have consequently found that the above-mentioned object can be achieved by using a mixed solvent of a polyhydric alcohol and water as a reaction solvent in a process for producing an N-long-chain acyl acidic amino acid by condensing an acidic amino acid or its salt with a long-chain fatty acid halide in the presence of alkali. This finding has led to the completion of the present invention.

That is, the present invention relates to a process for producing an N-long-chain acyl acidic amino acid or its salt, characterized in that an acidic amino acid or its salt is reacted with a long chain fatty acid halide containing from 8 to 22 carbon atoms in a solvent comprising a polyhydric alcohol and water.

The present invention also relates to a composition comprising an N-long-chain acyl acidic amino acid or its salt, characterized in that said composition is free of organic solvents and catalysts.

DESCRIPTION OF THE PREFERRED EMBODIMENTS

The acidic amino acid or its salt as one of the starting materials in the process of the present invention is preferably selected from glutamic acid, aspartic acid or salts thereof. These may be the optically active substances or racemic compounds. As examples of the salts, alkali metal salts such as the sodium salt, the potassium salt and the like can be mentioned.

The long chain fatty acid halide to be condensed with the acidic amino acid or its salt is a saturated or unsaturated fatty acid halide containing from 8 to 22 carbon atoms. Examples thereof include saturated or unsaturated fatty acid chlorides of a single composition, such as nonanoyl chloride, undecanoyl chloride, lauroyl chloride, tridecanol chloride, myristoyl chloride, palmitoyl chloride, stearoyl chloride and oleyl chloride; and mixtures of fatty acid chlorides such as coconut oil fatty acid chloride, tallow fatty acid chloride, hardened tallow fatty acid chloride, soybean fatty acid chloride and cottonseed fatty acid chloride.

Examples of the polyhydric alcohol used as a component of the reaction solvent in the present invention includes glycerol, ethylene glycol, propylene glycol, dipropylene glycol, 1,3-butylene glycol, sorbitol, mannitol, erythritol and pentaerythritol. Further, a polymer of the above-mentioned, such as polyethylene glycol or the like may also be used. Still further, non-reductive disaccharides containing plural hydroxyl groups, such as trehalose, sucrose and the like can also be included in the polyhydric alcohol of the present invention.

Even if these polyhydric alcohols remain in the desired product, they do not pose a problem in terms of safety or skin irritation. Further, most of these polyhydric alcohols are conventionally used as an ingredient which is incorporated into toiletries, surfactants or the like. Therefore the removal of the polyhydric alcohol is not required. Further, polyhydric alcohol does not have an objectionable odor. Accordingly, great industrial merits such as simplification of the procedure and of the equipment for removing the remaining solvent and catalyst and the like are provided.

Among the above-mentioned polyhydric alcohols, glycerol, ethylene glycol, propylene glycol, dipropylene glycol, and polyethylene glycol are preferred. From the aspects of the reaction yield, the low cost and the like, ethylene glycol, propylene glycol and dipropylene glycol are especially preferable in industrially practicing the process.

In the present invention, the reaction is conducted in the presence of an alkali. In a particularly preferred reaction procedure, the amino acid or its salt is dissolved in the polyhydric alcohol solution in the presence of an alkali first, then the long chain fatty acid halide is added. From the standpoint of increasing the reaction yield, the pH of the reaction solvent is preferably between 10 and 13. Further, it is advisable to conduct the reaction by maintaining the pH within this range until the reaction is completed. The alkali to be used is not particularly limited. Examples thereof include sodium hydroxide, potassium hydroxide, sodium carbonate and ammonia. Sodium hydroxide is especially practical.

The polyhydric alcohol in the reaction solvent used in the present invention can be used in a relatively wide range of concentrations. The concentration before the addition of the fatty acid halide is preferably between 5 and 80% in terms of percent by weight, more preferably between 5 and 50%. When it is less than 5%, the reaction yield is not as high. When it exceeds 80%, the acidic amino acid as a starting material is hardly dissolved in the reaction solvent.

The reaction temperature in the present invention is not particularly limited. The reaction is ordinarily performed at the range of from 0° C. to 50° C. However, in order to proceed with the reaction in a high yield, it is preferably from 0° C. to 40° C., more preferably from 5° C. to 30° C.

With respect to the ratios of the acidic amino acid or its salt and the long chain fatty acid chloride, it is preferable that the former is used in an equimolar or larger amount relative to the latter for obtaining the desired product in a high yield. Within this range, the larger the amount of the former, the more the yield is improved. Practically, it is preferable that the ratio (molar ratio) of the acidic amino acid or its salt relative to the long chain fatty acid chloride is between 1.0 and 1.5.

The concentration of the acidic amino acid or its salt is not particularly limited. In view of the increase in the reaction yield, it is preferably between 10 and 60% in terms of percent by weight before the addition of the fatty acid halide, and it is especially preferably between 15 and 50%.

In the reaction, it is preferable with respect to the reaction yield that the acidic amino acid or its salt is dissolved in a mixed solvent of water and a polyhydric alcohol, and a fatty acid halide is then gradually added to the solution while being stirred. The reaction time varies depending on conditions. The time of the addition of the fatty acid halide is usually between 1 and 6 hours, and the reaction time after the addition is usually between 10 minutes and 4 hours.

After the completion of the reaction, the reaction mixture is acidified with a mineral acid such as sulfuric acid, hydrochloric acid or the like, and the N-long-chain acyl acidic amino acid which is precipitated is separated through filtration. The N-long-chain acyl acidic amino acid separated through filtration is neutralized with a sodium hydroxide solution, a potassium hydroxide solution or the like, and water is then distilled off under reduced pressure to obtain an N-long-chain acyl acidic amino acid salt.

EXAMPLES

The present invention is illustrated specifically by referring to the following examples. However, the present invention is not limited thereto.

Example 1

Sodium L-glutamate monohydrate (175 g, 0.93 mols) was suspended in 230 ml of a 13% (by weight) dipropylene glycol aqueous solution, and 145 g of a 25% (by weight) sodium hydroxide aqueous solution was added thereto to prepare an aqueous solution having a pH of 12 (the concentration of dipropylene glycol is 9% by weight). To this aqueous solution was added 158 g (0.72 mols) of lauroyl chloride and a 25% (by weight) sodium hydroxide aqueous solution simultaneously over the course of 2 hours with stirring while maintaining a pH of 12 and a temperature of 10° C. Further, the reaction was conducted for 2 hours. After the completion of the reaction, the reaction mixture was adjusted to a pH of 1 with 15% (by weight) sulfuric acid, and crystals were precipitated with the addition of cold water. The crystals were collected through filtration, and dried at 25° C. for 24 hours. As a result, the amount of crystals was 220 g. By analyzing through HPLC, the yield of N-lauroyl glutamate was 89 mol % (relative to lauroyl chloride).

Example 2

Sodium L-glutamate monohydrate (175 g, 0.93 mols) was suspended in 230 ml of a 13% (by weight) polyethylene glycol aqueous solution, and 145 g of a 25% (by weight) sodium hydroxide aqueous solution was added thereto to prepare an aqueous solution having a pH of 12 (the concentration of polyethylene glycol is 9% by weight). The reaction was conducted as in Example 1. The crystals were collected through filtration, and dried at 25° C. for 24 hours. As a result, the amount of crystals was 220 g. By analyzing through HPLC, the yield of N-lauroyl glutamate was 85 mol % (relative to lauroyl chloride).

Example 3

Sodium L-glutamate monohydrate (175 g, 0.93 mols) was suspended in 250 ml of a 20% (by weight) polyethylene glycol aqueous solution, and 145 g of a 25% (by weight) sodium hydroxide aqueous solution was added thereto to prepare an aqueous solution having a pH of 12 (the concentration of polyethylene glycol is 14% by weight). The reaction was conducted as in Example 1. The crystals were collected through filtration, and dried at 25° C. for 24 hours. As a result, the amount of crystals was 223 g. By analyzing through HPLC, the yield of N-lauroyl glutamate was 91 mol % (relative to lauroyl chloride).

Example 4

Sodium L-glutamate monohydrate (175 g, 0.93 mols) was suspended in 230 ml of a 7.5% (by weight) sucrose aqueous solution, and 145 g of a 25% (by weight) sodium hydroxide aqueous solution was added thereto to prepare an aqueous solution having a pH of 12 (the concentration of polyethylene glycol is 5% by weight). The reaction was conducted as in Example 1. The crystals were collected through filtration, and dried at 25° C. for 24 hours. As a result, the amount of crystals was 223 g. By analyzing through HPLC, and the yield of N-lauroyl glutamate was 82 mol % (relative to lauroyl chloride).

Example 5

Sodium L-glutamate monohydrate (175 g, 0.93 mols) was suspended in 240 ml of a 15% (by weight) propylene glycol aqueous solution, and 140 g of a 25% (by weight) sodium hydroxide aqueous solution was added thereto to prepare an aqueous solution having a pH of 11 (the concentration of polyethylene glycol is 10% by weight). The reaction was conducted as in Example 1 with a pH of 11 at 20° C. using 170 g (0.78 mols) of lauroyl chloride. The crystals were collected through filtration, and dried at 25° C. for 24 hours. As a result, the amount of crystals was 235 g. By analyzing through HPLC, the yield of N-lauroyl glutamate was 90 mol % (relative to lauroyl chloride).

Example 6

Sodium L-glutamate monohydrate (175 g, 0.93 mols) was suspended in 240 ml of a 15% (by weight) glycerol aqueous solution, and 145 g of a 25% (by weight) sodium hydroxide aqueous solution was added thereto to prepare an aqueous solution having a pH of 12 (the concentration of glycerol is 10% by weight). The reaction was conducted as in Example 1. The crystals were collected through filtration, and dried at 25° C. for 24 hours. As a result, the amount of crystals was 200 g. These crystals were analyzed through HPLC, and the yield of N-lauroyl glutamate was 81 mol % (relative to lauroyl chloride).

Example 7

Propylene glycol was added to 200 ml of water, and a plurality of reaction solvents which differed by the concentration of propylene glycol were prepared. Sodium L-glutamate monohydrate (175 g, 0.93 mols) was suspended in each of the reaction solvents. Then, the reaction was conducted as in Example 1 using 160.9 g (0.72 mols) of coconut oil fatty acid chloride. The relationship between the concentration of propylene glycol before the addition of coconut oil fatty acid chloride and the yield of N-cocoyl glutamic acid is shown in Table 1.

TABLE 1

| Concentration of propylene glycol before addition of coconut oil fatty acid chloride (weight %) | Yield of N-cocoyl glutamic acid (mol %) |
|---|---|
| 0 | 74 |
| 5 | 79 |
| 9 | 88 |
| 10 | 91 |
| 12 | 92 |
| 40 | 94 |

Example 8

Organoleptic Evaluation of Odor.

The reaction was conducted as in Example 1 using a 13% ethanol aqueous solution as a reaction solvent to obtain crystals of N-lauroyl glutamate. These crystals were used as a Comparative Example. One hundred grams of N-lauroyl glutamate obtained in each of Examples 1, 2, 3, 4, 5 and 6 and the Comparative Example was dissolved in a 25% sodium hydroxide aqueus solution to prepare 450 g of a surfactant solution having a pH of 7.3. The odor was evaluated at 25° C. in this surfactant solution.

The evaluation scores were given to the surfactant solutions by ten panelists according to the folling standards, and the average values are shown in Table 2.

In accordance with the present invention, an acyl acidic amino acid or its salt can be produced in a high yield, and the need for equipment to remove organic solvents, catalysts and the like, which pose health and safety problems is eliminated. Thus, the process can be practiced industrially advantageously. Japanese Patent Application No. 22708/1997, filed on Feb. 5, 1997 and from which this application claims priority, is incorporated by reference herein.

What is claimed is:

1. A process for producing an N-long-chain acyl acidic amino acid or salt thereof, comprising reacting an acidic amino acid or a salt thereof with a long chain fatty acid halide containing from 8 to 22 carbon atoms in a solvent comprised of water and a polyhydric alcohol in the presence of an alkali.

2. The process of claim 1 wherein said acidic amino acid is selected from the group consisting of glutamic acid and aspartic acid.

3. The process of claim 1, wherein the salt of said acidic amino acid is selected from the group consisting of sodium, potassium and triethanolamine.

4. The process of claim 1, wherein said long chain fatty acid halide containing from 8–22 carbon atoms is selected from the group consisting of nonanoyl chloride, undecanoyl chloride, lauroyl chloride, tridecanol chloride, myristoyl chloride, palmitoyl chloride, stearoyl chloride, oleyl chloride, coconut oil fatty acid chloride, tallow fatty acid chloride, hardened tallow fatty acid chloride, soybean fatty acid chloride and cottonseed fatty acid chloride.

5. The process of claim 1, wherein said polyhydric alcohol is selected from the group consisting of glycerol, ethylene glycol, propylene glycol, dipropylene glycol, 1,3-butylene glycol, sorbitol, mannitol, erythritol, pentaerythritol, polyethylene glycol, trehalose and sucrose.

6. The process of claim 5, wherein said polyhydric alcohol is selected from the group consisting of glycerol, ethylene glycol, propylene glycol, dipropylene glycol and polyethylene glycol.

7. The process of claim 6, wherein said polyhydric alcohol is selected from the group consisting of ethylene glycol, propylene glycol and dipropylene glycol.

8. The process of claim 1, wherein said polyhydric alcohol comprises 5–80% by weight of said solvent.

9. The process of claim 8, wherein said polyhydric alcohol comprises 10–50% by weight of said solvent.

10. The process of claim 1, wherein the pH of said solvent is between 10 and 13.

11. The process of claim 1, wherein the reaction is carried out at a temperature of from 0° C. to 50° C.

12. The process of claim 11, wherein the reaction is carried out at a temperature of from 0° C. to 40° C.

13. The process of claim 12, wherein the reaction is carried out a temperature of from 5° C. to 30° C.

14. The process of claim 1, wherein said acidic amino acid or its salt is present in an amount of 10–60% by weight of said solvent.

15. The process of claim 14, wherein said acidic amino acid or its salt is present in an amount of 15–50% by weight of said solvent.

TABLE 2

| | Example 1 | Example 2 | Example 3 | Example 4 | Example 5 | Example 6 | Comparative Example |
|---|---|---|---|---|---|---|---|
| Score | 1.0 | 0.6 | 0.8 | 0.6 | 0.8 | 08 | 3.0 |

16. The process of claim 1, wherein the molar ratio of the acidic amino acid or its salt relative to the long chain fatty acid chloride is between 1.0 and 1.5.

17. The process of claim 1, wherein said acidic amino acid or its salt is dissolved in said solvent to form a solution and then said fatty acid halide is gradually added to this solution as it is being stirred.

18. The process of claim 15, wherein the fatty acid halide is added to said solvent over a period of time ranging from about 1 to 6 hours.

19. A composition comprising an N-long-chain acyl acidic amino acid or salt thereof which is the reaction product of an acidic amino acid or salt thereof with a long chain fatty acid halide containing from 8–22 carbon atoms, characterized in that said composition is free of organic solvents and catalysts.

20. The composition of claim 19, wherein said N-long-chain acidic amino acid is selected from the group consisting of glutamic acid and aspartic acid.

* * * * *

UNITED STATES PATENT AND TRADEMARK OFFICE
CERTIFICATE OF CORRECTION

PATENT NO.   : 6,060,613
DATED        : May 9, 2000
INVENTOR(S)  : Tatsuya Hattori et al.

Page 1 of 1

It is certified that error appears in the above-identified patent and that said Letters Patent is hereby corrected as shown below:

Title page,
Item [30], "May 2, 1997" should read -- Feb. 5, 1997 --.

Column 4,
Lines 50-51, "polyethylene glycol" should read -- sucrose --.
Line 65, "polyethylene" should read -- propylene --.

Column 5,
Line 56, "folling" should read -- following --.
Line 58, insert the following table:

|   -- | Score |
| --- | --- |
| No odor detected | 0 |
| Slight odor detected | 1 |
| Odor detected | 2 |
| Strong odor detected | 3    --. |

Signed and Sealed this

First Day of January, 2002

Attest:

Attesting Officer

JAMES E. ROGAN
Director of the United States Patent and Trademark Office